US009696563B2

(12) United States Patent
Trumm et al.

(10) Patent No.: US 9,696,563 B2
(45) Date of Patent: Jul. 4, 2017

(54) BRIGHTNESS-DEPENDENT ADJUSTMENT OF A SPECTACLE LENS

(71) Applicant: Rodenstock GmbH, Munich (DE)

(72) Inventors: Stephan Trumm, Munich (DE); Peter Seitz, Munich (DE); Rainer Sessner, Rothenburg ob der Tauber (DE); Adam Muschielok, Munich (DE); Helmut Altheimer, Baiswell-Lauchdorf (DE); Wolfgang Becken, Munich (DE); Andrea Welk, Munich (DE); Anne Seidemann, Munich (DE); Wolfgang Hauk, Munich (DE); Gregor Esser, Munich (DE)

(73) Assignee: Rodenstock GmbH, Munich (DE)

( * ) Notice: Subject to any disclaimer, the term of this patent is extended or adjusted under 35 U.S.C. 154(b) by 205 days.

(21) Appl. No.: 14/365,151

(22) PCT Filed: Dec. 13, 2012

(86) PCT No.: PCT/EP2012/005153
§ 371 (c)(1),
(2) Date: Jun. 13, 2014

(87) PCT Pub. No.: WO2013/087212
PCT Pub. Date: Jun. 20, 2013

(65) Prior Publication Data
US 2014/0340637 A1     Nov. 20, 2014

(30) Foreign Application Priority Data

Dec. 13, 2011    (DE) .................. 10 2011 120 974

(51) Int. Cl.
*A61B 3/14*     (2006.01)
*A61B 3/00*     (2006.01)
(Continued)

(52) U.S. Cl.
CPC ............... *G02C 7/027* (2013.01); *A61B 3/11* (2013.01); *A61B 3/112* (2013.01); *A61B 3/14* (2013.01);
(Continued)

(58) Field of Classification Search
USPC .................................................. 351/206, 246
See application file for complete search history.

(56) References Cited

U.S. PATENT DOCUMENTS

| 2009/0316112 A1 | 12/2009 | Neal et al. |
| 2010/0271596 A1 | 10/2010 | Legerton |
| 2011/0149239 A1 | 6/2011 | Neal et al. |

FOREIGN PATENT DOCUMENTS

| DE | 10313275 A1 | 10/2004 |
| JP | 2005-342153 A | 12/2005 |

(Continued)

OTHER PUBLICATIONS

International Search Report issued for PCT/EP2012/005153, Mar. 8, 2013.
(Continued)

*Primary Examiner* — Jack Dinh
(74) *Attorney, Agent, or Firm* — Schiff Hardin LLP

(57) ABSTRACT

Adjustment of an eyeglass lens or a pair of eyeglasses by means of an individual brightness-dependent centering of an eyeglass lens. In particular, a method for adjusting an individual eyeglass lens for at least one eye of an eyeglass wearer. The method includes defining an individual usage situation which includes at least one target brightness value for the light to be captured by the at least one eye; determining a position of the pupil in at least one direction of view of the at least one eye which occurs or is expected at the at least one target brightness value; determining a reference point of the eyeglass lens, in which the eyeglass
(Continued)

lens effects a required correction of individual refraction data for the at least one direction of view; on the basis of the determined individual value of the pupil position, providing and arranging the eyeglass lens in such a manner that the at least one reference point of the eyeglass lens is arranged in front of the at least one eye of the eyeglass wearer.

21 Claims, 2 Drawing Sheets

(51) Int. Cl.
  *G02C 7/02* (2006.01)
  *A61B 3/11* (2006.01)
  *G02C 7/06* (2006.01)
(52) U.S. Cl.
  CPC .............. *G02C 7/02* (2013.01); *G02C 7/06* (2013.01); *G02C 7/066* (2013.01)

(56) References Cited

FOREIGN PATENT DOCUMENTS

| | | |
|---|---|---|
| JP | 2006-514336 A | 4/2006 |
| JP | 2007-518500 A | 7/2007 |
| JP | 2008-502443 A | 1/2008 |
| JP | 2008-534051 A | 8/2008 |
| JP | 2009-537869 A | 10/2009 |
| JP | 2010-517089 A | 5/2010 |
| JP | 2010-524011 A | 7/2010 |
| JP | 2010-538325 A | 12/2010 |
| JP | 05-199996 B2 | 5/2013 |
| WO | WO-2006/101656 A2 | 9/2006 |
| WO | WO-2008/008999 A1 | 1/2008 |
| WO | WO-2010-083860 A1 | 7/2010 |
| WO | WO-2010-095938 A1 | 8/2010 |
| WO | WO-2011-042504 A1 | 4/2011 |

OTHER PUBLICATIONS

Office Action dated Sep. 4, 2015 for Japanese patent Application No. 2014-546357 (with English translation).

BRIGHTNESS-DEPENDENT ADJUSTMENT OF A SPECTACLE LENS

The present invention relates to the optimization and production of spectacle lenses for a spectacle wearer taking into consideration lighting conditions of an individual situation of wear, for which the respective spectacle lens is to be optimized.

For the production or optimization of spectacle lenses, in particular of individual spectacle lenses, each spectacle lens is manufactured such that the best possible correction of a refractive error of the respective eye of the spectacle wearer is obtained for each desired direction of sight or each desired object point. In general, a spectacle lens is said to be fully correcting for a given direction of sight if the values sphere, cylinder, and axis of the wavefront, upon passing the vertex sphere, match with the values for sphere, cylinder, and axis of the prescription for the eye having the visual defect. In the refraction determination for an eye of a spectacle wearer, dioptric values (particularly sphere, cylinder, cylinder axis) for a far (usually infinite) distance and optionally (for multifocal or progressive lenses) an addition for a near distance (e.g. according to DIN 58208) are determined. In this way, the prescription (in particular sphere, cylinder, cylinder axis, and optionally addition) that is sent to a spectacles manufacturer is stipulated. In modern spectacle lenses, object distances deviating from the standard, which are used in the refraction determination, can be indicated additionally.

However, a full correction for all directions of sight at the same time is normally not possible. Therefore, the spectacle lenses are manufactured such that they achieve a good correction of visual defects of the eye and only small aberrations in the main zones of use, especially in the central visual zones, while larger aberrations are permitted in peripheral zones.

In order to be able to manufacture a spectacle lens in this way, the spectacle lens surfaces or at least one of the spectacle lens surfaces is first of all calculated such that the desired distribution of the unavoidable aberrations is effected thereby. This calculation and optimization is usually performed by means of an iterative variation method by minimization of a target function. As a target function, particularly a function F having the following functional relation with the spherical power S, the magnitude of the cylindrical power Z, and the axis of the cylinder a (also referred to as "SZA" combination) is taken into account and minimized:

$$F = \sum_{i=1}^{m} [g_{i,S\Delta}(S_{\Delta,i} - S_{\Delta,i,target})^2 + g_{i,Z\Delta}(Z_{\Delta,i} - Z_{\Delta,i,target})^2 + \ldots].$$

In the target function F, at the evaluation points i of the spectacle lens, at least the actual refractive deficits of the spherical power $S_{\Delta,i}$ and the cylindrical power $Z_{\Delta,i}$ as well as target specifications for the refractive deficits of the spherical power $S_{\Delta,i,target}$ and the cylindrical power $Z_{\Delta,i,target}$ are taken into consideration.

It was found in DE 103 13 275 that it is advantageous to not indicate the target specifications as absolute values of the properties to be optimized, but as their deviation from the prescription, i.e. as the required misadjustment. This has the advantage that the target specifications are independent of the prescription ($Sph_V$, $Zyl_V$, $Axis_V$, $Pr_V$, $B_V$) and that the target specifications do not have to be changed for every individual prescription. Thus, as "actual" values of the properties to be optimized, not absolute values of these optical properties are taken into account in the target function, but the deviations from the prescription. This has the advantage that the target values can be specified independent of the prescription and do not have to be changed for every individual prescription.

The respective refractive deficits at the respective evaluation points are preferably taken into consideration with weighting factors $g_{i,S\Delta}$ and $g_{i,Z\Delta}$. Here, the target specifications for the refractive deficit of the spherical power $S_{\Delta,i,target}$ and/or the cylindrical power $Z_{\Delta,i,target}$, particularly together with the weighting factors $g_{i,S\Delta}$ and $g_{i,Z\Delta}$, form the so-called "design" or spectacle lens design. In addition, particularly further residues, especially further parameters to be optimized, such as coma and/or spherical aberration and/or prism and/or magnification and/or anamorphic distortion, etc., can be taken into consideration, which is particularly implied by the expression "+ . . . ". Thus, the design of a spectacle lens in particular specifies the way the aberrations are distributed on the spectacle lens. Preferably, it is specified for a plurality of evaluation points on the spectacle lens how large the aberration to be obtained and optionally its weighting in the target function are to be.

Preferably, the design of a spectacle lens also comprises a setting of the position of one or more marked points, in particular reference points, such as the position of a distance reference point and/or of a near reference point and/or of a prism reference point and/or of a centration point and/or of a position or a course of a principal line of sight. While in the beginning of progressive lenses spectacle lenses were specified by the spectacle lens manufacturer in a graded fashion according to different categories, the adaptation of spectacle lenses for individual spectacle wearers has been individualized increasingly throughout the years. Specifically, the spectacle lens designs have taken into account individual conditions, such as dimensions and position of the individual spectacles frame (e.g. forward inclination, face form angle), habitual parameters (e.g. head posture, head movement), an individual situation of wear (individual object distance model), or individual anatomical conditions (e.g. corneal vertex distance).

In addition to the design of the spectacle lens, the correct centration is of importance as well. For example, for the adaptation of spectacles—in addition to other parameters—mainly the pupillary distance for far vision (far PD) is measured. In the case of progressive lenses, usually—also for otherwise highly individualized lenses—the far PD is measured and for the determination of the near PD or the course of the main line of sight a simplified model (rotation of the eye around a point) and standard parameters (usually the eye radius from the Gullstrand model, cf. DIN 5340) are used. The far PD is measured approximately with most conventional video centration systems by setting a visual task for a specified distance to the device, which is considered to be sufficiently large.

To further improve an individual adaptation of a spectacle lens or spectacles, even more detailed models for describing the eye's anatomy and the muscular system moving the eye have been considered as well. For example, different axes with different radii can be set for horizontal and vertical rotations. Moreover, it is possible to distinguish between the mechanical and the optical ocular centers of rotation. Despite the efforts made to determine the individual eye movement as precisely as possible, the quality of the individual adaptation of a spectacle lens or spectacles is limited.

For adapting spectacles, in addition to other parameters, in particular the position of the pupil (pupillary distances and fitting heights) for far vision under generally undefined lighting conditions has so far been measured manually or by means of video centration systems. The actual sizes or positions of the pupils for the lighting conditions prevailing in the later use of the spectacles are not taken into consideration here.

It is the object of the present invention to achieve an improvement of the individual adaptation of spectacle lenses. This object is solved by methods having the features indicated in claim 1 or 2 and by a measuring apparatus having the features indicated in claim 12. Preferred embodiments are subject of the dependent claims.

According to one aspect, the invention provides a method for adapting, in particular optimizing and producing, an individual spectacle lens for at least one eye of a spectacle wearer, comprising in particular collecting individual data for the least one eye of the spectacle wearer. Here, collecting individual data comprises specifying an individual situation of wear, which comprises at least one brightness target value for the light to be captured by the at least one eye in the intended situation of wear, in which the spectacle lens is to be used. A target value of the (medium) luminance is preferably specified as the brightness target value. Preferably, the individual situation of wear also specifies an object distance model at least partly, i.e. it specifies the distance from objects expected in the individual situation of wear of a spectacle lens to be adapted for at least one or several directions of sight. For a progressive lens, for example, at least the expected object distance for a direction of sight corresponding to a distance reference point of the spectacle lens and for a direction of sight corresponding to a near reference point of the spectacle lens is specified.

Further, the method (in particular collecting individual data) comprises determining an individual position, occurring or expected for the at least one brightness target value, of the pupil of the at least one eye for at least one direction of sight of the at least one eye, i.e. in at least one eye position. That is, what is determined is the individual position of the pupil resulting for the at least one eye of the spectacle wearer for the target value, specified in the individual situation of wear, of the (medium) luminance detected by the eye. In particular two alternative approaches are preferred here.

In one of these preferred approaches, the individual position of the pupil is detected (directly or indirectly), while the at least one eye is subjected to the specified brightness target value. That is, the brightness condition expected in the later actual situation of wear is set during the detection of the pupil position in the at least one direction of sight.

In another preferred approach, a formal relation between brightness and the position of the pupil of the at least one eye is specified. Further, the brightness acting on the eye during the detection of the position of the pupil is detected. This is followed by a corresponding correction of the position of the pupil for transformation to the brightness target value by means of the specified relation between brightness and the position.

Specifying the at least one brightness target value is preferably performed by a user input, either directly as a numerical value or by selection from among predetermined numerical values or from a predetermined value range, or by selection from predetermined application fields for which typical brightness values are deposited (e.g. differentiation between day and night spectacles for vehicle drivers; outdoor sports, computer work, etc.). So far, such situations of wear have been occasionally distinguished in the typical object distances, but the brightness and its individual influence on the position of the pupil to be expected in the individual case have not been taken into consideration. Thus, in the measurement of the eyes, in particular for a centration, attention has so far not been paid to the actual brightness prevailing during the measurement.

In the present invention, however, it has been found that by considering the actual brightness in the individual situation of wear and its individual influence on the position of the pupil, in particular in an asymmetrical adaptation of the pupil for different brightnesses, an improvement of the individual adaptation of spectacle lenses is easily achieved already in the centration of a spectacle lens alone, but preferably also in the optimization and production of a spectacle lens.

The method further comprises determining a reference point of the spectacle lens, in which the spectacle lens causes a correction of individual refraction data required for the at least one direction of sight. The requirement of correction is preferably specified by a target function, in which individually determined refraction data, in particular for different directions of sight (e.g. as refractive power course), together with tolerances or specifications for deviations from the full correction (the so-called design) are taken into account. Depending on the intended application, the refraction data is collected preferably even for a plurality of directions of sight. Thus, for a multifocal lens or a progressive lens, preferably at least one distance refraction and one near refraction of the at least one eye are detected, from which in particular also the required addition results for a progressive lens.

For every direction of sight, the required optical power of the spectacle lens to be optimized and produced depends on the distance of the objects in the intended situation of wear. The distance is described by the predetermined object distance model preferably for every situation of wear. A distance reference point and/or a near reference point and/or a centration point of the spectacle lens can e.g. be selected as at least one reference point. The individual refraction to be at least partly corrected in the at least one reference point can either be measured directly for the spectacle wearer (e.g. for the distance or the near reference point) or be derived from measured values for other directions of sight e.g. from a desired course of a power increase between distance and near zones (e.g. for a reference point deviating from the distance or the near reference point).

Moreover, the method comprises providing and arranging the spectacle lens (in particular fitting the spectacle lens in the frame) such that the at least one reference point of the spectacle lens (e.g. the centration point) is arranged depending on the determined individual value of the position of the pupil, in front of the at least one eye of the spectacle wearer. In particular, in other words, the spectacle lens is provided and arranged (or designed for arrangement) such that in the individual situation of wear, when looking in the at least one direction of sight for which the individual value of the position of the pupil (i.e. the individual position of the pupil) was determined, the spectacle wearer looks through the determined reference point of the spectacle lens. Thus, preferably a centration point of the spectacle lens used as a reference point is arranged horizontally in front of the position of the pupil predetermined or to be expected for the specified brightness target value particularly for a view in the at least one direction of sight. In particular for the fitting of the lens in the spectacles frame, a centration of the spectacle lens depending on the brightness occurring in the individual situation of wear is performed.

While so far for the centration of the spectacle lens attention has not been paid to neither the brightness at the moment the centration data (e.g. pupillary distance or fitting height) is measured nor to the brightness for the desired situation of application, an individual brightness-dependent centration is performed according to the invention by determining and considering the individual influence of the brightness on the pupil position.

In the following, centration does not only mean the positioning of the spectacle lenses in the frame, but preferably also the location of the design points with respect to each other and preferably even the course of the principal line of sight.

In a further aspect of the invention, even the individual brightness-dependent position of the pupil is taken into account in the optimization of a spectacle lens. In this aspect, the invention thus provides a method for optimizing and producing an individual spectacle lens for at least one eye of a spectacle wearer, comprising specifying an individual situation of wear, which specifies a brightness target value for the light to be captured by the at least one eye for at least two different reference points of the spectacle lens. Data of wear describing the individual situation of wear comprises a value for the brightnesses to be expected. In this way, a brightness-dependent consideration of the position of the pupil for various directions of sight is performed in the optimization and production of a spectacle lens. Here, the brightness expected (specified) in the individual situation of wear may well be the same for all directions of sight (in particular for the two reference points). It is preferably sufficient to specify one single brightness target value that can then be applied to all reference points.

Further, the method comprises determining refraction data of the at least one eye for the at least two different reference points and thus in particular for a plurality of object distances, in particular for at least two viewing zones or directions of sight, which in particular correspond to far vision and near vision.

The reference points in particular of a progressive lens could preferably be a distance reference point and a near reference point. Here, in particular different brightness target values in the individual situation of wear are specified for the distance and near reference points. The different brightness in the individual situation of wear occurring in the distance and near reference points can individually lead to different positions and/or sizes of the pupil. To take this into account in the optimization and production of the spectacle lens, in particular these reference points are adapted according to the individual, brightness-dependent pupil position, i.e. in particular shifted based on a target design (starting design) created without considering a dependence of the pupil position on the brightness.

A differentiation between distance and near vision is particularly desired for progressive spectacle lenses. In this case, preferably different refraction data results for the at least two reference points. Considering the individual influence of the brightness on the position of the pupil in the optimization process is also advantageous for reference points in which same refraction data of the eye are to be corrected. Thus, the approach according to the invention provides an improvement of the individual adaptation in particular also for individually calculated (optimized) single-vision lenses.

To this end, the method comprises determining an individual influence of the brightness of the light captured by the at least one eye on the position of the pupil of the at least one eye and optimizing and producing the spectacle lens, which causes a correction, destined for the reference points, of the refraction data for the positions of the pupil of the at least one eye, which result from the determined influence of the brightness on the position of the pupil for the brightness target values specified for the reference points.

In the present invention, it has been found that an improvement of the individual adaptation of spectacles or a spectacle lens can be obtained by performing a brightness-dependent centration and/or optimization in a way in which in particular individual, non-symmetrical changes of a pupil in an adaptation to the brightness (adaptation) are at least partly considered.

Optimizing the spectacle lens preferably comprises minimizing a target function, in particular according to the above-mentioned target function F. Particularly preferably, the method comprises determining an individual position and/or size of the pupil respectively occurring or expected for the specified brightness target values, wherein optimizing the spectacle lens comprises minimizing a target function which, for the at least two reference points, evaluates a correction of the refraction data respectively determined for the respective reference point, said correction being caused by the spectacle lens in a surrounding of the respective reference point, wherein in particular the size of the surrounding of the respective reference point is selected depending on the individual size of the pupil determined for the respective reference point. Thus, the target function is evaluated preferably in a known manner on the vertex sphere of a model describing the system of object, spectacle lens, and eye. Here, the power of the spectacle lens is calculated preferably by means of ray tracing and/or wavefront tracing starting from an object point through the spectacle lens up to the vertex sphere, and is combined with the eye's refractive error projected onto the vertex sphere in the target function. Particularly preferably, the evaluation of the wavefront for a principal ray passing through the respective reference point is performed in a surrounding of the principal ray which depends on the corresponding pupil size. Thereby, in particular higher-order aberrations are corrected particularly well according to the real situation of wear. Possible approaches for considering higher-order aberrations in particular according to further preferred embodiments of the present invention will be described in more detail further below. For example, higher-order aberrations can be measured individually be means of an aberrometer, for example. In another preferred embodiment, which will be described in detail further below, such aberrations can be obtained from statistical data in particular in dependence on other individually determined parameters.

In a preferred embodiment, the individual position of the pupil for the situation of wear is taken into consideration by the method comprising: determining, in particular measuring a position of a reference point of the eye for directions of sight that correspond to the at least two reference points of the spectacle lens, i.e. for directions of sight through the respective reference point of the spectacle lens to be optimized and produced. In a preferred embodiment, the reference point of the eye is a point that does not shift relative to the retina when the brightness changes. Particularly preferably, the positions of the apex of the eye are directly or indirectly determined as the reference point, i.e. the apex positions can be measured directly or positions of another point are measured, the position thereof relative to the apex being known.

Preferably, optimizing comprises, for each reference point of the spectacle lens, calculating the course of a principal ray such that it passes through the respective position of the reference point of the eye in a (individual) situation of wear of the spectacle lens, which is preferably also specified by data of wear. The course of the principal rays, i.e. a principal ray iteration (ray tracing) as preferably used in conventional optimization methods as well, is performed preferably independent of the individual, brightness-dependently influenced pupil position in this embodiment. Here, the individual pupil position is considered preferably by calculating a wavefront (wavefront tracing) in a surrounding of the respective principal ray such that the position of the surrounding relative to the principal ray is determined and considered according to the determined individual influence of the brightness on the position of the pupil. In particular, in the model of the ray course, on which the calculation is based, an aperture stop (entrance pupil of the eye) is used, the position of which relative to the principal ray having an individual shift depending on the brightness. In this embodiment, the wavefront is evaluated not necessarily in a surrounding centered around the principal ray, but in an individually shifted surrounding.

In this preferred embodiment, the positions of the reference points for different directions of sight can be determined in particular together with further rotation parameters of the eye without the brightness prevailing during this measurement having to be known. To nevertheless know the necessary reference of the pupil position to the reference point of the eye, the determination of an individual influence of the brightness of the light captured by the at least one eye on the position of the pupil of the at least one eye preferably comprises determining the position of the pupil relative to the reference point of the eye for the at least one brightness target value, preferably for all specified brightness target values. As explained above, this determination can be performed either by a direct measurement with the respective brightness target value or, for example, by interpolation or extrapolation on the basis of models and/or measurements with other brightnesses.

In a further preferred embodiment, the individual position of the pupil for the situation of wear is taken into consideration by the method comprising: determining, in particular measuring a position of the pupil of the eye for directions of sight that correspond to the at least two reference points of the spectacle lens, i.e. for directions of sight through the respective reference point of the spectacle lens to be optimized and produced. Since the position of the pupil preferably depends on the brightness and this individual dependence is to be taken into consideration, the respective position of the pupil is determined for a determined or determinable brightness. In a preferred embodiment, during this process, the brightness is set according to the respectively specified brightness target value. In another preferred embodiment, the brightness is measured during the measurement only as well. From an individual influence of the brightness on the position of the pupil, which is determined particularly by a separate measurement, a position correction of the respective pupil position is performed for the different directions of sight based on the measured pupil position in this case.

Preferably, optimizing in this preferred embodiment comprises, for each reference point of the spectacle lens, calculating the course of a principal ray such that it passes through the respective, optionally corrected position of the pupil of the eye in a (individual) situation of wear of the spectacle lens, which is preferably also specified by data of wear.

Thus, if the measurement of the pupil position for the different directions of sight has been performed with the target brightness (brightness target value), preferably the directly measured position values will be taken into account. If, however, measurements have been performed with a different brightness, then the pupil position for the purpose of principal ray iteration will be corrected preferably according to the individual influence of the brightness.

The course of the principal rays, i.e. a principal ray iteration (ray tracing) as preferably used in conventional optimization methods as well, is performed depending on the individual, brightness-dependently influenced pupil position in this embodiment. On the basis of this principal ray tracing, preferably a calculation of a wavefront (wavefront tracing) in a surrounding of the respective principal ray is performed, with its position preferably not depending on the brightness. The size of this surrounding, however, preferably depends individually on the brightness in the way described above. In particular, in this embodiment, an aperture stop (entrance pupil of the eye) is used in the ray course model underlying the calculation, the position of the aperture stop being centered preferably with respect to the principal ray.

Preferably, determining the expected individual position of the pupil and/or determining the individual influence of the brightness on the position and/or size of the pupil comprises:
  setting measurement conditions in which the brightness captured by the at least one eye at least corresponds to a brightness target value specified in the individual situation of wear;
  detecting the position and/or size of the pupil of the at least one eye (as the expected individual value) under the measurement conditions set.

In an alternative preferred embodiment, determining the expected individual position of the pupil and/or determining the individual influence of the brightness on the position and/or size of the pupil comprises:
  specifying (defining) a relation (e.g. as an analytical description in the form of a mathematical formula) between the brightness captured by the at least one eye and the position and/or size of the pupil, wherein the specified relation has at least one individual (i.e. to be individually identified) adaptation parameter (also referred to as a free parameter or fit parameter);
  identifying (in particular measuring) a position and/or size of the pupil together with a brightness captured by the at least one eye. That is, the (average) brightness (or the brightness to which the pupil of the at least one eye has adjusted) prevailing during the measurement is detected as an essential part of the measurement conditions.
  determining the at least one individual adaptation parameter from the identified position and/or size of the pupil as well as the brightness identified therewith; and
  identifying the individual position and/or size of the pupil expected for the predetermined brightness target value (or the predetermined brightness target values) from the specified relation between the brightness captured by the at least one eye and the position and/or size of the pupil taking the determined individual adaptation parameter into account.

In a preferred embodiment, the brightness captured by the at least one eye, which is determined together with a position and/or size of the pupil, is measured (in particular) directly by means of a brightness sensor.

In a in particular alternative preferred embodiment, identifying a position and/or size of the pupil together with a brightness captured by the at least one eye comprises:

arranging a brightness reference object close to the at least one eye such that the brightness reference object is subjected to the same brightness as the at least one eye;

collecting image data of the at least one eye together with the brightness reference object (e.g. in one single shot, or—if flashlight is used—preferably in direct succession, wherein the brightness reference object is captured without flashlight); and determining the brightness from the representation of the brightness reference object in the image data.

Preferably, determining the expected individual position of the pupil and/or determining the individual influence of the brightness on the position and/or size of the pupil comprises measuring a position of the pupil relative to a coordinate system fixed with respect to the head. Preferably, the measurement is performed by means of a video centration system and using extrinsic features (e.g. spectacles frame, marks on the spectacles frame or on a clip-on element). Depending on whether this measurement is performed within the scope of a preferred alternative described above, preferably the expected position for the specified brightness target value will be measured, or a position for an arbitrary brightness together with the brightness prevailing here will be measured, from which the at least one adaptation parameter for the predetermined relation will be determined subsequently. This approach is particularly preferred if the measurement of the position and/or size of the pupil is performed by means of a video centration system, which in addition also identifies further individual parameters (for example with respect to the selected spectacles frame) for the spectacle lens adaptation.

Preferably, determining the expected individual position of the pupil and/or determining the individual influence of the brightness on the position and/or size of the pupil comprises measuring a position of the pupil relative to a marked feature of the at least one eye.

Preferably, determining the expected individual position of the pupil and/or determining the individual influence of the brightness on the position and/or size of the pupil comprises specifying a direction of sight by means of a fixation object and/or a fixation target.

In a preferred embodiment, a measurement of a position and/or size of the pupil is performed for a first luminance in the range from approximately 3 cd/m$^2$ to approximately 30 cd/m$^2$, and a measurement of a position and/or size of the pupil is performed for a second luminance (different from the first one) in the range from approximately 0.003 cd/m$^2$ to approximately 30 cd/m$^2$, preferably in the range from approximately 0.003 cd/m$^2$ to approximately 3 cd/m$^2$, particularly preferably in the range from 0.003 cd/m$^2$ to approximately 0.3 cd/m$^2$, most preferably in the range from approximately 0.003 cd/m$^2$ to approximately 0.03 cd/m$^2$.

In a further aspect, the invention provides a measuring apparatus for collecting individual user data that specifies at least a position of a pupil of at least one eye, wherein the measuring device comprises an illuminating device adapted to determine a brightness captured by the at least one eye. This can be done in particular in two alternative, preferred ways. The illuminating device is either adapted to control the brightness such that a predetermined brightness is achieved, or the illuminating device comprises a sensor that measures the brightness causes by the (possibly non-controllable) illuminating device and possible ambient light.

Further, the measuring apparatus comprises an image-capturing device adapted to collect image data of the pupil together with a position reference point, its position relative to the eye, in particular to the retina, not depending on the brightness. The invention thus offers the possibility of collecting user data that comprises a direct influence of the brightness on the position and/or size of the pupil of at least one eye. This data can then be used to achieve a better adaptation of spectacles or a spectacle lens.

The measuring apparatus preferably comprises a brightness sensor adapted to measure the brightness captured by the at least one eye. Further preferably, the measuring apparatus comprises a data-of-wear detection interface for detecting a specification for at least one brightness target value and an illumination control device adapted to control the brightness of the illuminating device such that the light captured by the at least one eye corresponds to the detected brightness target value.

In a further aspect, the measuring apparatus is not required to comprise its own illuminating unit. Instead, the ambient brightness can be used and measured by means of a brightness sensor. In this case, the measuring apparatus comprises:

a brightness sensor adapted to measure the brightness captured by the at least one eye; and an image-capturing device adapted to collect image data of the pupil together with a position reference point.

Preferably, the measuring apparatus comprises a fixation target and/or a fixation object and/or a fixation projection device for controlling the eye's direction of sight, i.e. in particular a light-emitting device for controlling or directing the direction of sight of at least one eye. Particularly preferably, the fixation target and/or the fixation object and/or the fixation projection device is formed by the illuminating device, wherein the brightness captured by the eye, which influences the position and/or size of the pupil, is mainly provided by the fixation target and/or the fixation object and/or the fixation projection device. Particularly preferably, the illumination control device thus controls the brightness of the fixation target and/or the fixation object and/or the fixation projection device. In the detection of the position and/or size of the pupil or the image data of the pupil by means of the measuring apparatus, the relevant brightness at the eye or the brightness of the fixation target and/or the fixation object and/or the fixation projection device or the brightness of the illuminating device is detected and particularly stored as well.

Preferably, the measuring apparatus is designed as a video centration system and/or as an auto refractometer and/or aberrometer and/or keratograph and/or tonograph and/or pachymeter.

In a further aspect, the invention provides a computer program product, in particular in form of a storage medium or a sequence of signals, comprising computer-readable instructions, which, when loaded in a storage of a computer, preferably in the storage of a data-processing unit of an apparatus according to the present invention, in particular in one of the preferred embodiments described herein, and executed on the computer (in particular the apparatus), cause the computer (in particular the apparatus) to perform a method according to the present invention, in particular according to a preferred embodiment thereof.

After the measurement principle according to an aspect of the invention has been described by way of preferred embodiments, various aspects of preferred approaches particularly in view of applications of these measurements will be discussed in the following. Finally, it will be shown exemplarily how the collected data can be preferably used in order to adapt the centration and in particular the design of the spectacle lenses, i.e. in particular to optimize a spectacle lens individually.

In one aspect, the invention provides considering the position and/or size of the pupil under the conditions actually present in the future application. Here, conditions is understood to be also at least the brightness in the desired application situation. In addition, other stimuli that may influence the position and/or size of the pupil can be used as well. This relates e.g. to the accommodation of the eye at defined distances (e.g. at infinity, in the near zone, or fogged) as well as to special fixation or vergence positions (e.g. monocular or binocular convergence by eye movement control via fixation targets or near vision samples).

The measurements required for this are preferably performed with an apparatus according to the invention, which is particularly preferably designed as a video centration system, i.e. exhibits the functionality of a video centration system, wherein preferably at least one of the measurements can also be used for determining centration data or further individual parameters. These can be supplemented or replaced by measurements with other ophthalmic optics devices.

For the required referencing of different measurements among each other with respect to the pupil measurements, in particular with respect to the determinations of the position of the pupil, marked features of the eye, a fixation of the direction of sight, or referencing measurements can be used. A detection of the position and/or size of the pupil for a specified condition according to the invention can be performed by direct measurement of these parameters under said condition (e.g. the specified brightness) or by calculation from measurements at conditions different therefrom (e.g. other brightnesses).

Here, the size of the pupil is preferably defined and determined according to one of the following ways:
  area of the actual pupil;
  area of the incircle or circumcircle of the actual pupil;
  area of the circle describing the actual pupil margin best;
  weighted area of the actual pupil. The weighting is preferably performed as a function of the distance from a marked point for emphasizing special regions. A thus marked point is preferably the pupil center in particular according to one of the following definitions or the corneal vertex.

Instead of the circle, other geometrical shapes (e.g. ellipses) can be used as well.

The position of the pupil is preferably understood to be a marked point of the pupil in particular according to one of the following definitions:
  center of the actual pupil area;
  center point of the circle describing the actual pupil margin best;
  center of the weighted area of the actual pupil. The weighting is preferably performed as a function of the distance from a marked point for emphasizing special regions. A thus marked point is preferably the pupil center according to one of the above definitions (e.g. for emphasizing the central region) or the corneal vertex.

As mentioned above, in a preferred embodiment, the conditions (e.g. lighting conditions) corresponding to the future situation of wear are already created during the measurement of an individual position and/or size of the pupil by means of a video centration system. These measurements, in particular image data collected here, can also be used for determining centration data and individual data.

Additional images (image data) can be created with the video centration system for further defined conditions (e.g. lighting conditions) corresponding to those of the future application, and in particular be evaluated according to the position and/or size of the pupil without going through a complete evaluation in the meaning of a video centration.

In another preferred embodiment of collecting individual user data, a priori undefined conditions (e.g. lighting conditions) can be used as well, which can be measured where required for the respective application. To this end, illuminating devices, such as fixation targets (i.e. direction of sight-controlling light fields) or fixation objects for specifying a direction of sight, which are present on the apparatus anyway, or special illuminating devices of a video centration system can be used or provided. Of course, external illuminating devices, which may also be part of the store equipment of an optician, can be used as well. The same applies to fixation targets, objects, and projections. A fixation projection is understood to be the imaging system typically used in ophthalmic optics devices, the image of which is fixed by the viewer or to which image the viewer accommodates.

In the practical application of a video centration system with the optician, it is often difficult to ensure the necessary brightness conditions at the location of the video centration, which should correspond exactly to the situation of wear actually expected for the spectacle wearer. For example, video centration systems are often located in a sales room that cannot be darkened. Therefore, a further embodiment of a method for determining an individual position of the pupil, occurring or expected for the at least one brightness target value, for at least one direction of sight of the at least one eye uses at least one further measuring apparatus with which the position of the pupil in particular with respect to a marked feature of the eye can be detected. Such an apparatus in conformity with a preferred embodiment of the invention comprises at least one image-capturing device (camera) adapted to detect at least parts of the pupil margin. Further, the measuring apparatus preferably comprises an (internal or external) illuminating device with which defined brightness conditions can be created, i.e. the measuring apparatus is preferably adapted to control the brightness of the illuminating device.

Preferably, the measuring apparatus comprises a shading element for shading the eye region in order to be able to create a surrounding with little brightness for the eye even in a bright environment. Alternatively, the measuring apparatus can also be set up in a darkened room (e.g. refraction room of an optician) or a separated part of a room.

For controlling the direction of sight, the measuring apparatus preferably has a fixation target and/or a fixation object and/or a fixation projection device, which is in particular adapted to create a virtual target. In a particularly preferred embodiment, the measuring apparatus is at the same time (i.e. integrally) designed as an auto refractometer and/or aberrometer and/or keratograph and/or tonograph and/or pachymeter.

The combination with a video centration measurement is not absolutely necessary for the centration or optimization of spectacle lenses. Instead, the changes in position and/or size of the pupil can be determined only with one measuring apparatus as provided by the present invention, and the fitting position of the lens can be determined in a different way (e.g. manual centration according to Viktorix) independent thereof.

Irrespective of whether the determination of an individual position and/or size of the pupil, occurring for at least one brightness value, or the determination of an individual influence of the brightness on the position and/or size of the pupil is performed by means of a video centration system equipped according to the invention or by means of another measuring apparatus according to the invention, the measurement of the brightness at the location of the test person (spectacle wearer), in particular at the location of the eye (i.e. the brightness detected by the eye—also referred to as the "relevant brightness"), is preferably performed according to one of the following possibilities.

According to a preferred embodiment, the measuring apparatus (e.g. video centration system) comprises a wired or wireless brightness sensor that measures the relevant brightness or the brightness at a point from which it is possible to calculate back to the relevant brightness.

In another preferred embodiment, the relevant brightness is determined by means of a brightness reference object detected in image data together with the at least one eye of the spectacle wearer by an image-capturing device. From the brightness of the brightness reference object in the image data, conclusions about the relevant brightness can be drawn.

To avoid false measurements due to reflection or similar effects when a brightness reference object is used, an object as homogenous as possible and scattering in a diffuse way is preferably used. The spatial expansion is preferably selected such that the image of the object comprises at least the number of pixels that allows a determination of the brightness with the required precision. The spectral characteristic is preferably selected such that conclusions about the relevant brightness can be drawn taking into account the spectral characteristic of the camera or the individual color channels.

In the simplest case, such a brightness reference object can be made of a piece of white (or colored) paperboard or plastics. This piece can also be configured to be adhesive in order to be easily attachable to the spectacles frame or the test person in a simple and comfortable way.

Advantageously, extrinsic position reference marks disposed on the spectacles frame or a clip-on bracket can be designed such that they can be used as brightness reference objects in conformity with this invention. Thereby, recordings both for determining the position of the ocular center of rotation and for determining the position and/or size of the pupil under conditions of wear can be used in a particularly advantageous way, and thus both parameters can be determined with few recordings. In most of the video centration systems on the market, clip-on brackets are used for the geometrical calibration of camera recordings. These can also be provided with such a brightness reference object.

Moreover, the selected frame can be used as a brightness reference object as long as its spectral characteristic is sufficiently known or determined in advance. The brightness reference object can also be installed in a stationary way in the store of the optician at a position at which it appears in the recording and allows drawing conclusions about the relevant brightness. Further possible brightness reference objects represent the features of the person which are either known or are only subject to little variation among different test persons. An example of this is the sclera.

The relevant brightness is calculated from the brightness value of the pixels in the recording, which represent the brightness reference object, taking the spectral characteristic of the brightness reference object and the camera sensitivity of the relevant brightness into account. In many cases, the measurement recordings are lightened by flash lighting. Due to the time scales, such additional lighting mostly does not have any influence on the pupil size or position. The captured brightness of the brightness reference object is influenced by the flash lighting though. In this case, the brightness reference object for determining the brightness can be captured in a prior or subsequent recording without flashlight, i.e. with the brightness to which the pupil has adjusted in size and position.

In the determination of the individual position of the pupil for different conditions (e.g. brightness, accommodation state), it is important to be able to determine the different positions of the pupil relative to each other. To make this possible, different preferred embodiments for measurement methods that can be combined with each other will be suggested in the following. This makes particularly sense if different apparatuses are used.

In a preferred embodiment, the position of the pupil is referenced by a marked features of the eye, which is independent of the brightness in particular with respect to a direction of sight. Preferably, as the marked feature, an intrinsic feature, such as structures on the conjunctiva or cornea as well as the limbus, or an extrinsic one, such as a reflex of a definedly applied illuminating device on the cornea or lens (e.g. "Purkinje reflex") is used.

If the same marked feature of the eye is detected when several apparatuses are used (e.g. at least one measurement with a video centration system and at least one measurement with another measuring apparatus according to the invention in one of the described preferred embodiments), the positions of the pupil determined relative thereto under different conditions can be used and calculated without any additional matching. Such features are preferably the above-mentioned intrinsic features and reflexes, which are based on geometrically equivalent arrangements of the corresponding illuminating devices.

In another preferred embodiment, the position of the pupil is referenced by fixation of the direction of sight. If the position of the head does not change between individual measurements relative to the image-capturing device, the positions in the image coordinate system of the individual recordings relative to each other can be used directly as well. However, this requires the direction of sight to be fixed or controlled or measured. If the direction of sight is constant, the relative data can be used directly. In the case of possible changes of the directions of sight between the individual recordings, their effect can be compensated for.

For controlling the direction of sight, preferably fixation objects or fixation targets (i.e. light fields directed in at least one plane) are used. For measuring the direction of sight, known methods of direction of sight determination (e.g. measurement of the Purkinje reflexes) can be used.

If the position of the head changes relative to the image-capturing device between individual measurements (for example if several apparatuses are used), this will preferably be compensated for by specifying the positions of the head by at least one non-eye intrinsic or extrinsic feature.

In a further preferred embodiment, the position of the pupil is referenced by measurements with the same brightness. If e.g. different marked features of the eye (e.g. different intrinsic features or reflexes with a different geometry of the illuminating units) are used in the measurement with a video centration system and a different independent inventive measuring apparatus in particular according to a preferred embodiment, referencing can be performed by making at least one recording with both systems under the same conditions—within the scope of the required accuracy.

Thereby, the position of the respective marked features with respect to each other can be via the positions of the pupil, identified for this common condition, relative to the position of the corresponding marked feature of the eye. This common condition does not necessarily have to be known. However, it may be—e.g. to avoid recording with an additional condition in the further course—one of the conditions used later.

In a further preferred embodiment, the position of the pupil is inferred from the size of the pupil. In particular, first of all an individual relation between the pupil size and the pupil position is determined preferably by means of a measuring apparatus according to the invention. Preferably, an analytical (e.g. linear) model with at least one free parameter adaptable to the individual measurement is assumed for this relation. Preferably, this determined individual relation is then applied to further measurements in particular by means of other measuring systems (e.g. in a video centration system). In this way, for example from image data determined with a video centration system at a brightness not known before, conclusions can be drawn on the brightness prevailing during the measurement and the correction of the pupil position required for a correct centration at the brightness expected in the situation of wear by evaluation of the pupil size.

In the simplest case, the position and/or size of the pupil is/are measured under the conditions desired for the optimization or centration of the lenses, i.e. conditions corresponding to the future situation of wear. However, it is also possible to determine positions and/or sizes for individual conditions for which no direct measurements exist. Preferably, even continuous distributions across at least regions of the spectacle lens are determined and used. In this way, preferably a distance-dependent brightness with a resulting distance-dependent pupil in progressive lenses analogous to the power distribution between near and distance points is taken into consideration.

Preferably, parameters for a (e.g. analytically given) model are obtained from at least one measurement of the position and/or size of the pupil. Such a model, together with the at least one individually determined parameter, preferably describes an individual influence of the brightness of the light captured by the at least one eye on the position and/or size of the pupil. Preferred models are, for example, linear or logarithmic dependencies, dependencies with a free parameter, as well as interpolations or extrapolations between or via at least two support values. If there are more measurements than free parameters of the model, adaptation calculations (e.g. smallest squared deviations) can be performed to increase the precision or statistical reliability.

In a preferred embodiment, as the model for the size of the pupil (radius d in mm) in dependence on the brightness (luminance B in mL) there is used:

$$\log(d)=a-b(\log(B)+c)^3$$

The values a=0.8558, b=0.000401, and c=8.1 can be considered as an average for a majority of spectacle wearers. As part of preferred embodiments of the invention, values for the parameters a, b and/or c can be adapted by at least one measurement with at least one known brightness, or preferably even be determined completely by three or more measurements with known brightnesses.

A linear relation between the position and the size of the pupil is assumed as a preferred example of a model of the position of the pupil, the coefficients of which being determined preferably individually. Preferably, a coefficient of approximately −0.07 to approximately 0.14 millimeters shift of the pupil per millimeter dilatation (change in size of the pupil) is specified or determined. Here, a positive value means a nasal shift upon contraction. Preferably the above model can be assumed for the pupil size.

Preferably, further stimuli (e.g. accommodation and focusing, direction of sight and vergence, etc.) that may influence the position and/or size of the pupil can are taken into consideration as well. The stimuli can be provided either monocularly or binocularly as well as in arbitrary combinations. For example, the specified individual situation of wear primarily comprises at least one brightness target value and thus describes the lighting conditions in the intended individual use of the spectacles. In a preferred embodiment, a measurement in the range of the photopic brightness (lumincances in the range from approximately 3 $cd/m^2$ to approximately 30 $cd/m^2$) and one in the range of the mesopic brightness (luminaces in the range from approximately 0.003 $cd/mn^2$ to approximately 30 $cd/m^2$) are performed. They can be supplemented by measurements at the boundaries between the ranges and in the scotopic range (luminances in the range from approximately $3\cdot10^{-6}$ $cd/m^2$ to approximately 0.03 $cd/m^2$).

In the consideration of accommodation and focusing, real objects (e.g. fixation objects or near vision tests) or images (e.g. the projection systems on the basis of a slide or CCD used in ophthalmic optics devices) can be used, for example. Thereby, the accommodation of the eye at predetermined distances (e.g. at infinity, in the near zone, or "fogged" i.e. non-accommodateable) can be controlled.

Moreover, for controlling the direction of sight or for creating special fixation or vergence positions, real objects (e.g. fixation objects, near vision tests), images, or fixation targets (i.e. light fields polarized in at least one plane) can be used. Here, rolling can be considered as well.

The thus obtained information on the position and/or size of the pupil are now in particular used for centering and/or optimizing the spectacle lenses. Some possibilities that may also be combined will be explained in the following.

For example, the actual position is considered in the determination of the geometrical location of the visual points. In the simplest case, the thus obtained information on the position and/or size of the pupil is used for determining the position of individual reference or visual points (such as the near or distance reference points). This can also be achieved by correcting other determined parameters, such as the fitting height and monocular pupil distance. In a preferred embodiment, the near or distance reference point is assigned specific brightnesses and/or accommodation states.

In particular in relation with a model for describing the influence of the brightness on the position and/or size of the pupil, the exact course (horizontal and vertical) of the principal line of sight in progressive lenses can be completely optimized in every point according to the locally provided conditions (e.g. accommodation state or brightness). Particularly preferably, in the optimization of a spectacle lens, the actual position and/or size of the pupil under the provided conditions (e.g. accommodation state or brightness) is/are taken into consideration.

As pointed out further above, the invention provides the possibility, in one aspect, of taking into account the pupillary play (i.e. in particular the preferably individual dependence of the size and/or position of the pupil on the individual situation of wear) and the associated change in refraction (or the refraction dependent thereon) of the eye in the optimization and production of spectacle lenses, without the higher-order aberrations (HOA) of the individual eye having to be known or measured individually. Conventionally, the latter are determined with a complex wavefront measuring apparatus, which is often not available.

The development of individually optimized spectacle lenses, in particular of progressive lenses, allows considering individual features of the spectacle wearer, such as pupillary distance, corneal vertex distance, and individual position of wear of the spectacles. The latest spectacle lens generation is even capable of additionally considering, in the optimization of the lenses, higher-order aberrations (HOA) forming upon the refraction of light on the boundary surfaces of the spectacle lens and the eye.

In a preferred embodiment of the present invention, the optimization of such spectacle lenses includes in particular the propagation and refraction of a wavefront individually determined for each eye, said wavefront extending across a preferably individually determined pupil and being comprised of both higher-order aberrations (HOA) and lower-order aberrations (LOA). Both the LOA and the HOA of the spectacle lens are influenced by the position of wear of the spectacle lens and are taken into account in the optimization; likewise, the HOA and the LOA of the eye and the subjectively determined refraction are taken into account in the optimization.

Since the wavefront tracing is inseparably connected with the pupil size, it is also taken into account in the optimization of the spectacle lens. Here—due to physiological phenomena, such as light reaction of pupil near reaction—the pupil size occurring in the situation of wear may be a function of one or more variables, such as the direction of sight, convergence, brightness of the observed scene and/or the object distance. In particular in this respect is an improvement of the adaptation of a spectacle lens achieved by an individual consideration of the position and/or size of the pupil according to the invention. To determine not only the position and/or size of the pupil, but also the wavefront individually, an aberrometer could be used, for example. Such devices are usually expensive for an optician and therefore not very common, but they provide a very precise possibility for determination of the individual wavefront aberration of the eye.

As mentioned above, in one aspect, the invention provides an alternative approach that allows making the advantages of the latest spectacle lens technology widely available without an aberrometer being necessary. As already pointed out, the higher-order aberrations (HOA) of the individual eye do not have to be known or measured individually. This is achieved in particular by doing without an individual wavefront measurement and by replacing the individually determined wavefront and possibly also the individually determined pupil size, which are required for the optimization of the lenses, by model assumptions. By means of the model assumptions used in the method described here, it is also achieved that—compared to a conventional spectacle lens—the probability that an individual person is supplied well with a spectacle lens is increased. Thus, a method according to this aspect of the invention improves the care of a group of persons with spectacle lenses overall.

For a more detailed description of this aspect of the invention, some terms will be used in the following which in particular are to be understood as follows:

The term "data" (date of a group of eyes or of an individual eye) preferably refers to at least one type of the following data: wavefront data, brightness, pupil data, refraction data "other data". The individual types of data will be explained in the following.

For example, the "wavefront data" describes the wavefront determined in particular in a wavefront measurement (or on the basis of a model assumption according to the invention). They are preferably available as coefficients of the Zernike polynomials, so-called Zernike coefficients, at a defined pupil size and include lower-order aberrations (LOA), such as in particular prism, sphere, astigmatism, and higher-order aberrations (HOA), such as in particular trefoil, coma and/or spherical aberration. The Zernike coefficients can be indicated for a standard pupil size, which may differ from the actually (individually) determined or measured pupil size.

"Brightness" in particular refers to the luminance of the light incident on or captured by the eye.

"Pupil data" characterizes the entrance pupil of the eye and comprises in particular the pupil parameter of pupil size (e.g. pupil radius or pupil diameter) and preferably also one or more of the following data: pupil center (e.g. location of the center of the pupil area relative to the apex), amplitude of the hippus, and changes in the pupil with changing brightness of the surrounding. The pupil size and preferably also the pupil center must be available in the wavefront measurement; however, this and other pupil data can also be determined with other measuring apparatuses. In particular, the pupil size available in the pupil data may differ from the standard pupil size for which the Zernike coefficients of the wavefront data are indicated.

The "refraction data" preferably includes sphere, cylinder, axis for the visual distance infinity or for a different visual distance at which the refraction has been performed, as well as addition, or sphere, cylinder, axis, which are determined at a finite reading distance (e.g. 40 cm). Sphere, cylinder, and axis may also be present as so-called power vectors in an equivalent representation.

In the following, the above-mentioned "other data" of the eye is understood to be at least one type of the following data: brightness incident on the eye (or captured by the eye) in the refraction (or refraction determination), brightness incident on the eye (or captured by the eye) in the measurement of pupil data, accommodation state of the eye, as well as age of the eye (i.e. age of the spectacle wearer).

Thus, in one aspect, the invention provides a method for optimizing and producing a spectacle lens for at least one eye of a spectacle wearer, preferably according to one of the above-described aspects. The method comprises providing a distribution of data, in particular measured data, of a plurality of eyes which in particular do not include the at least one eye of the spectacle wearer. This data of the plurality of eyes form in particular at least a part of a (statistical) set of data, which as a basis for a statistical model describes relations between different physical and/or physiological parameters. To this end, the data differs in the distribution of data, or the eyes of the plurality of eyes differ at least partly in physical and/or physiological parameters. The distribution of data can be available as a sample or in the form of analytical models.

In a preferred embodiment, providing a distribution of data comprises providing a distribution of higher-order aberrations (HOA) of a plurality of eyes, which preferably depends on the parameters pupil data and/or refraction data and/or other data.

Further, in this aspect of the invention, the method comprises providing (in particular measuring) or determining physical and/or physiological data for the at least one eye of the spectacle wearer. Preferably, providing or determining physical and/or physiological data for the at least one eye of the spectacle wearer comprises providing (in particular measuring) or determining refraction data of the at least one eye in particular for at least two different reference points, preferably according to at least some of the above-described details of the further aspects of the present invention. Here, the provided (in particular measured) or determined physical and/or physiological data can in particular directly relate to or comprise such parameters on which the provided distribution of the data of a plurality of eyes depends directly, or these parameters are determined from the provided (in particular measured) or determined physical and/or physiological data by means of further functional relations, as will be described in more detail further below on the basis of preferred embodiments.

According to this aspect, the method further comprises determining most probably data of the at least one eye with at least one physical and/or physiological condition. In particular, from the provided (in particular measured) or determined physical and/or physiological data (conditions) for the at least one eye of the spectacle wearer and/or from further physical and/or physiological conditions (in particular concerning an individual situation of wear), conclusions are drawn on the values of this data most possible according to the provided (statistical) distribution of the data for the at least one eye. In a preferred embodiment, conclusions are drawn on the most probable wavefront data of the at least one eye of the spectacle wearer with at least one pair of pupil data and accommodation state. The thus determined most probable data can then be used directly or indirectly in the calculation or optimization of the spectacle lens.

Even if for this aspect of the invention, according to which use is made of a (statistical) model (or statistical models) instead of an individual measurement of data, the above-discussed improvements and simplifications result especially in the determination of wavefront data, this aspect of the invention is not limited to the use in relation with wavefront data. Other (statistical) relations between physical and/or physiological data or parameters can also be used in this way for determining corresponding individual data. This relates particularly to a determination of an expected individual position of the pupil and/or a determination of an individual influence of the brightness of the light captured by the at least one eye on the position of the pupil of the at least one eye and/or a determination of the individual size of the pupil occurring or expected for the specified brightness target values. Here, the data to be determined is determined on the basis of the statistical set of data from individually determined parameters for the eye of the spectacle wearer.

Further details in particular on preferred embodiments of the invention will be described by way of example in the following with reference to the accompanying drawings FIG. 1 is a schematic illustration of the course of a method according to a preferred embodiment of the present invention;

Figure 1:
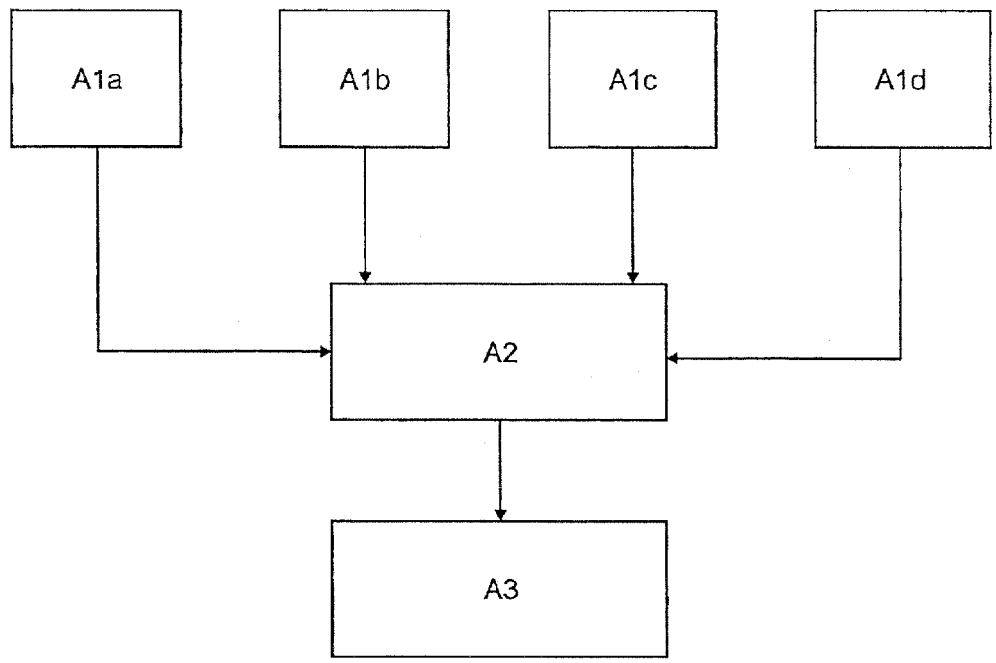

In a preferred embodiment, the method (in particular a method for adapting an individual spectacle lens or a method for optimizing and producing a spectacle lens) in particular comprises the method steps illustrated in FIG. 1, which will be explained in the following.

Step A1$a$: providing a distribution of the data of a group (plurality) of eyes, which depends on physical and/or physiological parameters. The distribution of the data of a group of eyes can be provided as a sample or in the form of analytical models. It represents the statistical information known for a group of eyes. This provided distribution of data is therefore also referred to as a statistics data set. Possible data of a group of eyes is, for example, wavefront data, brightness, pupil data, refraction data, or other data of eyes, as well as combinations thereof. Preferably, also the statistical relations between at least one component of this data and at least a further influencing variable, in the following referred to as a parameter, are represented in the distribution. The parameters can be of a physical or physiological nature. Possible parameters are pupil data, refraction data, brightnesses, other data, or combinations thereof.

A possible analytical model of such a distribution according to a preferred embodiment is composed of a vector-valued regression function and a multivariately normally distributed regression error. Both the regression function and the covariance matrix of the regression error is a vector or matrix-valued function of at least one of the parameters. The regression function and the covariance matrix are typically obtained by minimizing the error squares of a sample weighted with the covariance matrix.

Each component of the regression function can be in the form of a polynomial of the parameters, which is defined section by section, and indicate the average dependence of the type of data, assigned to this component, on the parameters. In particular, such a function may, in sections, be a constant function, a linear function, or a quadratic function of the parameters. The multivariately normally distributed regression error may, but does not have to, posses a non-diagonal covariance matrix that can also be a function of the parameters. Such a function (i.e. each element of the covariance matrix), like the regression function itself, can in sections be approximated as a constant function, linear function, or quadratic function of the parameters. If in particular the regression error does not depend on the parameters, then the covariance matrix will be a constant function of the parameters. If there are no statistical relations between individual components, then the covariance matrix will be diagonal.

Step A1$b$: providing physical and/or physiological data of an individual eye. In this step, physical and/or physiological data of an individual eye for which the spectacle lens is to be calculated is provided.

Step A1$c$: optionally providing most probable data WD1 of said one eye, which corresponds to one or more parameters of the distribution of step A1$a$. If required, the most probable data WD1 of the eye for which a spectacle lens is to be calculated is provided. This most probable data of the eye corresponds to one or more parameters on which the distribution provided in step A1$a$ depends.

Step A1$d$: optionally providing at least one functional relation between the parameters of the distribution provided in step A1$a$ and the data of the eye provided in step A1$b$ and/or in step A1$c$. If in the following step A2 a statistical relation between one or more parameters of the distribution provided in step A1$a$ and one or more physical and/or physiological data provided in step A1$b$ or the most probable data provided in step A1$c$ is required but it is not possible to establish a direct statistical relation, then a functional relation needs to be provided in addition. The functional relation can be obtained from additional sources and represents an average statistical relation.

Step A2: drawing conclusions about the most probable data W2 of said one eye under at least one physical and/or physiological condition. If required, first of all (one or more) functional relations of step A1$d$ are used to convert data and/or most probable data WD1 provided for the eye in step A1b or A1c into the parameters on which the distribution provided in step A1a depends.

Next, preferably a conditional distribution of the data of a group of eyes is calculated by evaluating the distribution of data provided in step A1a on the data of the eye provided in step A1b and/or the most probable data WD1 provided in step A1c, which were optionally calculated in advance by means of the functional relations provided in step A1d.

If the distribution of the data of a group of eyes is given as a sample, then the conditional distribution will be that part of the sample the parameters of which differ sufficiently little from the data provided in step A1b and/or the most probable data WD1 provided in step A1c. If the distribution of the data of a group of eyes is given as an analytical approximation, then the conditional distribution will be calculated by inserting the most probable data WD1 and/or the physical and/or physiological data of said one eye into the analytical approximation. If the distribution of the data of the group of eyes is in particular given as a regression model, then the conditional distribution of the data will result from the insertion of the data or most probable data WD1 of said eye into the regression function and into the covariance matrix.

Preferably, the conditional distributions of the data provided in step A1a result analogously with one or more physical and/or physiological conditions, which are required for the calculation of the spectacle lens. To this end, the previously determined conditional distribution is evaluated under the respective physical and/or physiological conditions. The most probable data WD2* of said one eye under these conditions is given by the maxima of this conditional distribution. The above calculated most probable data WD2* can be completed to form the most probable data WD2 of said one eye taking into consideration the data provided in steps A1b and A1c.

Step A3: directly or indirectly using the most probable data WD2 of said one eye from step A2 in the calculation or optimization of the spectacle lens. The most probable data WD2 of said one eye determined in the preceding step is now used in the calculation of a spectacle lens. This can either be done directly, so that step A3 includes the calculation of the spectacle lens. But in addition to the most probable data WD2, other information, such as the individually determined refraction of the eye, is taken into account as well. The most probable data WD2 can also indirectly be taken into account in the calculation of the spectacle lens by being used in a further method step similar to the step A1c.

Figure 2:
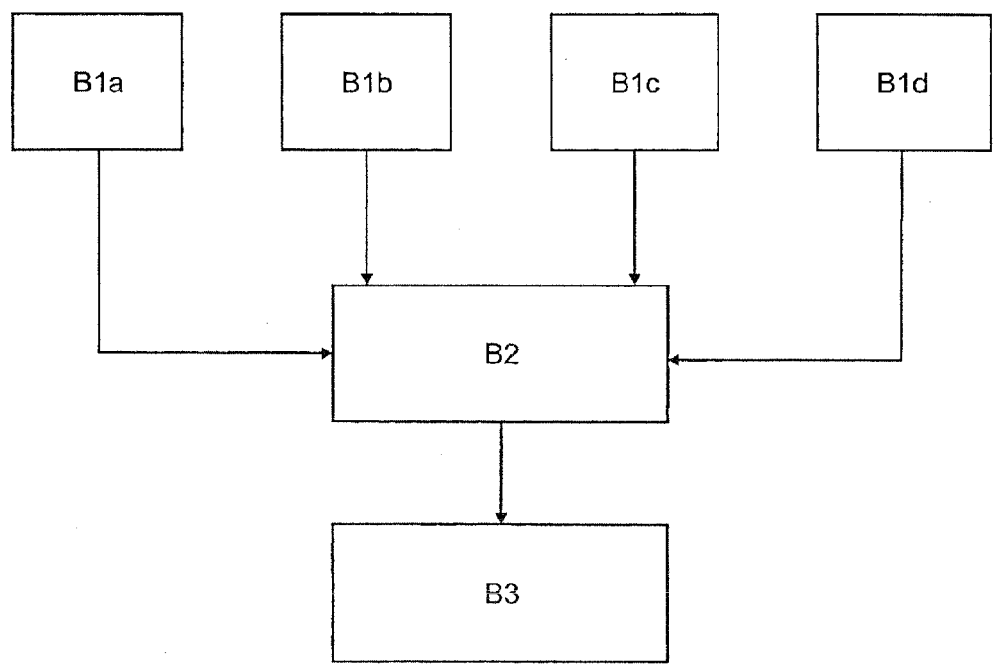
FIG. 2 is a schematic illustration of the course of a method according to a further preferred embodiment of the present invention.

A further preferred embodiment of a method, which in particular is considered a preferred special case of the method described with respect to FIG. 1, will be described in the following with reference to FIG. 2. The here-described method in particular comprises the method steps illustrated in FIG. 2.

Step B1a: providing a distribution of the HOA of a group of eyes, which preferably depends on the parameters pupil data and/or refraction and/or other data. The distribution can be a sample or in the form of analytical models. It represents the statistical information, known for a group of eyes, on the Zernike coefficients of the higher-order aberration (HOA) indicated for a standard pupil. If possible, the statistical relations between at least one Zernike coefficient indicated for a standard pupil and at least one further influencing variable, in the following referred to as a parameter, are to be represented in the distribution as well. Possible parameters are pupil data, refraction data and/or other data.

A possible analytical model of such a distribution is composed of a vector-valued regression function and a multivariately normally distributed regression error. Both the regression function and the covariance matrix of the regression error is a vector or matrix-valued function of at least one of the following parameters: pupil parameter, of the refraction data in power vector representation, the addition, age, accommodation state, LOA of the Zernike coefficients scaled to a standard pupil. The refraction data may be subjectively determined refraction data, or also objective refraction data determined as the Zernike coefficient and pupil sizes in a suitable way. The regression function and the covariance matrix are typically obtained by minimizing the error squares of a sample weighted with the covariance matrix.

Each component of the regression function can be in the form of a polynomial of the parameters, which is defined section by section, and indicate the average dependence of the Zernike coefficient, assigned to this component, on the parameters, wherein the Zernike coefficient is indicated for a standard pupil. In particular, such a function may, in sections, be a constant function, a linear function, or a quadratic function of the parameters. The multivariately normally distributed regression error may, but does not have to, posses a non-diagonal covariance matrix that can also be a function of the above-mentioned parameters. Such a function (i.e. each element of the covariance matrix), like the regression function itself, can in sections be approximated as a constant function, linear function, or quadratic function of the parameters. If in particular the regression error does not depend on the parameters, then the covariance matrix will be a constant function of the parameters. If there are no statistical relations between individual Zernike coefficients, then the covariance matrix will be diagonal.

A preferred special case of such an analytical model is the distribution of the Zernike coefficients $C_3^{-3}$ to $C_5^5$, wherein the components of the regression function are constant for all coefficients except for $C_4^0$, and the component corresponding to the spherical aberration $C_4^0$ is a piecewise linear function of the age. The distribution of said Zernike coefficients is preferably a multivariate normal distribution centered around the averages given by the regression function, wherein said multivariate normal distribution may posses a different standard deviation for each component and its covariance matrix is diagonal.

Such a model can in particular be determined from the data published by Salmon et al. (e.g. in "Normal-eye Zernike coefficients and root-mean-square wavefront errors", J Catatact Refract Surg, Bd. 32, p. 2064-2074, 2006), wherein left eyes can be transferred into right eyes by mirroring on the vertical, and the averages apply to right eyes. The Zernike coefficients of the radial order 3 to 5 are indicated for a pupil diameter of 5 mm and an accommodation of 0 dpt:

$$C_3^{-3} = -0.02359 \pm 0.044 \, \mu m$$

$$C_3^{-1} = -0.02315 \pm 0.0536 \, \mu m$$

$$C_3^1 = -0.00179 \pm 0.0439 \, \mu m$$

$$C_3^3 = -0.00001 \pm 0.0352 \, \mu m$$

$$C_4^{-4} = -0.00223 \pm 0.0153 \, \mu m$$

$$C_4^{-2} = -0.00323 \pm 0.0107 \, \mu m$$

$$C_4^0 = \begin{cases} 0.05052 \pm 0.0321 \, \mu m & \text{age} < 45 \text{ years} \\ 0.05052 \, \mu m + 0.05 \, \mu m \cdot (\text{age} - 45 \text{ years})/15 \text{ years} \pm 0.0321 \, \mu m & 45 \text{ years} \le \text{age} \le 60 \text{ years} \\ 0.10052 \pm 0.0321 \, \mu m & \text{age} > 60 \text{ years} \end{cases}$$

-continued $$C_4^2 = 0.00114 \pm 0.0184 \, \mu m$$

$$C_4^4 = 0.00476 \pm 0.0168 \, \mu m$$

$$C_5^{-5} = -0.00222 \pm 0.00765 \, \mu m$$

$$C_5^{-3} = 0.00247 \pm 0.00765 \, \mu m$$

$$C_5^{-1} = -0.00628 \pm 0.00765 \, \mu m$$

$$C_5^{1} = -0.00021 \pm 0.00612 \, \mu m$$

$$C_5^{3} = -0.00003 \pm 0.00459 \, \mu m$$

$$C_5^{5} = 0.00001 \pm 0.00765 \, \mu m$$

wherein the notation $C_n^m = \langle C_n^m \rangle \pm \sigma_{C_n^m}$ is an abbreviated notation for a normal distribution around the average $\langle C_n^m \rangle$ with a given standard deviation $\sigma_{C_n^m}$. In the present case, the regression function is given by the vector of the averages of the Zernike coefficients ($\langle C_3^{-3} \rangle$, $\langle C_3^{-1} \rangle$, ..., $\langle C_5^3 \rangle$, $\langle C_5^5 \rangle$), wherein all averages except for $\langle C_4^0 \rangle$ are constants, and $\langle C_4^0 \rangle$ depends on the age in the above-described way. Here, the covariance matrix is a quadratic diagonal matrix with the squared standard deviations of the respective Zernike coefficients as diagonal elements $\text{Diag}(\sigma_{C_3^{-3}}^2, \sigma_{C_3^{-1}}^2, \ldots, \sigma_{C_5^3}^2, \sigma_{C_5^5}^2)$. Here, all averages of the Zernike coefficients are constant functions of the accommodation state, but the model could be easily expanded upon availability of corresponding Zernike coefficients depending on the accommodation state of the eye.

Step B1b: providing the refraction data of an eye and preferably other data of this eye. The refraction (sphere, cylinder, axis, at a distance and/or near, as well as the addition) of an eye, which is detected by the optician, ophthalmologist, optometrist, or an apparatus as a standard, is provided and converted into the power vector notation if required. If possible, other data is collected as well, for example accommodation state of the eye and/or age of the eye.

Step B1c: providing the most probable pupil data of the same eye for at least one brightness. The most probable pupil data of a specific eye, including pupil size and preferably pupil position relative to the apex, is provided. Preferably, this is done in the method illustrated in this document (see in particular the corresponding details for determining the most probable pupil data of a specific eye according to the preferred embodiment described further below in particular with reference to FIG. 3).

As far as possible, the most probable pupil data is based on measurements of the present eye. If not sufficient measurements are available, or if they are too imprecise, then the most probable pupil data will be determined from the distribution of the possible pupil data, which may depend on the refraction data and/or the other data of the eye (see auxiliary method). The most probable pupil data consists of numerical values (pupil size and optionally pupil position relative to the apex) for each individual brightness, or it is available as a function of the brightness.

The distribution of the possible pupil data represents the pupil data considered possible, wherein the distribution is based on measurements of the present eye as far as possible. The width of the distribution (standard deviation) corresponds to the standard error of the measurements. If not enough precise or too few measurements are available, then the distribution of the possible pupil data of the present eye will be supplemented with a distribution of the pupil data of a group of eyes, which may depend on the refraction data and/or other data of the eye (see in particular the corresponding details relating to the determination of the most probable pupil data of a specific eye according to the embodiment described further below in particular with respect to FIG. 3).

The most probable pupil data is given for at least one brightness, which will be required later in the optimization of the spectacle lens in step B3 or which is present during the refraction of said one eye. In particular, at least one brightness means a continuum of brightnesses, so that the most probable pupil data and preferably the distribution of the possible pupil data can be indicated with these for any arbitrary brightness.

Step B1d: optionally providing at least one functional relation between the parameters of the distribution provided in B1a and the data provided in B1b. If in the further step (B2) a statistical relation between an influencing variable (e.g. the addition) and the HOA is required but it is not possible to establish a direct statistical relation between this influencing variable and the HOA, as e.g. no connected sample of this influencing variable and the HOA exists, then a functional relation between said influencing variable and another influencing variable (e.g. the age) needs to be provided in addition, wherein there has to be a direct statistical relation between said one and the other influencing variable.

A possible functional relation is the one of age and accommodation width in presbyopia, the so-called Duane curve. It can be taken from Atchison and Smith ("The aging eye", in Optics of the Human Eye, Edinburgh, Elsevier Science Ltd., 200, pp. 221-233), for example. If one resorts to the common practice of selecting the addition to be ⅔ of the accommodation width, a functional relation between addition and age between 45 and 60 years will result:

age=59.2 years+5.77 years/dpt·(addition+$AN$), where AN is the multiplicative inverse of the near refraction distance, usually −2.5 dpt. A further functional relation is the one of accommodation state of the eye and the refraction data.

Step B2: drawing conclusions about the most probable wavefront data of said one eye for at least one pair of pupil data and accommodation state. If required, first of all (one or more) functional relations of step B1d are used to convert data provided for the eye in step B1b into the parameters on which the distribution provided in step B1a depends. For example, the addition included in the refraction data needs to be converted into an age if the distribution of the pupil data in step B1a is according to age, and the addition of said one eye included in the refraction data in step B1b was provided.

Next, a conditional distribution of the HOA of a group of eyes is calculated by evaluating the distribution of HOA provided in step B1a at the refraction data of the eye and/or the other data of said one eye provided in step B1b and/or the most probable pupil data of this eye provided in step B1c, which were optionally calculated in advance by means of the functional relations provided in step B1d. The conditional distribution of the HOA is usually given for a standard pupil.

If the distribution of the HOA of a group of eyes is given as a sample, then the conditional distribution will be that part of the sample the data of which (most probable pupil data and/or refraction data and/or other data) is sufficiently close to the data of said one eye. If the distribution of the HOA of a group of eyes is present as an analytical approximation, then the conditional distribution will be calculated by inserting the most probable pupil data and/or the refraction data and/or the other data of said eye into the analytical approximation. If the distribution of the HOA is in particular given as a regression model, then the conditional distribution of the HOA will result from the insertion of the data of said eye into the regression function and into the covariance matrix.

The conditional distribution of the HOA at one or more accommodation states of the eye, which will be required later in step B3 for optimization, analogously result from an evaluation of the conditional distribution of the HOAs with corresponding accommodation states. The most probable HOAs for the respective accommodation states are given by the maximum of this conditional distribution.

To calculate the most probable wavefront data for the desired accommodation states and pupil data, lower-order aberrations (LOA) need to be determined in addition to the respective HOAs. Here, the LOAs are adapted for the most probable HOAs for the respective accommodation state such that an objective refraction calculated based on suitable metrics from the LOAs, the most probable HOAs and the most probable pupil data present for the refraction is identical with the subjective refraction provided in step B1$b$.

The thus collected most probable wavefront data is finally indicated for the pupil data required for the calculation or optimization of the spectacle lens (step B3). This pupil data was provided as most probable pupil data in step B1$c$. This step particularly includes rescaling of the Zernike coefficients to the given pupil sizes. The most probable wavefront data is now available for at least one pair of pupil data and accommodation state.

Step B3: optimizing a spectacle lens by using the refraction data, the most probable pupil data, and the most probable wavefront data. In this step, common methods are used for optimizing the spectacle lens by taking into account the refraction data, the wavefront data, and the pupil data. Here, the wavefront data is given by the most probable wavefront data determined in step B2, and the pupil data is given by the most probable pupil data determined in step B1$c$. The thus optimized spectacle lens improves the probability of a good ophthalmic care of said eye and improves the ophthalmic care of a group of persons overall.

Figure 3:
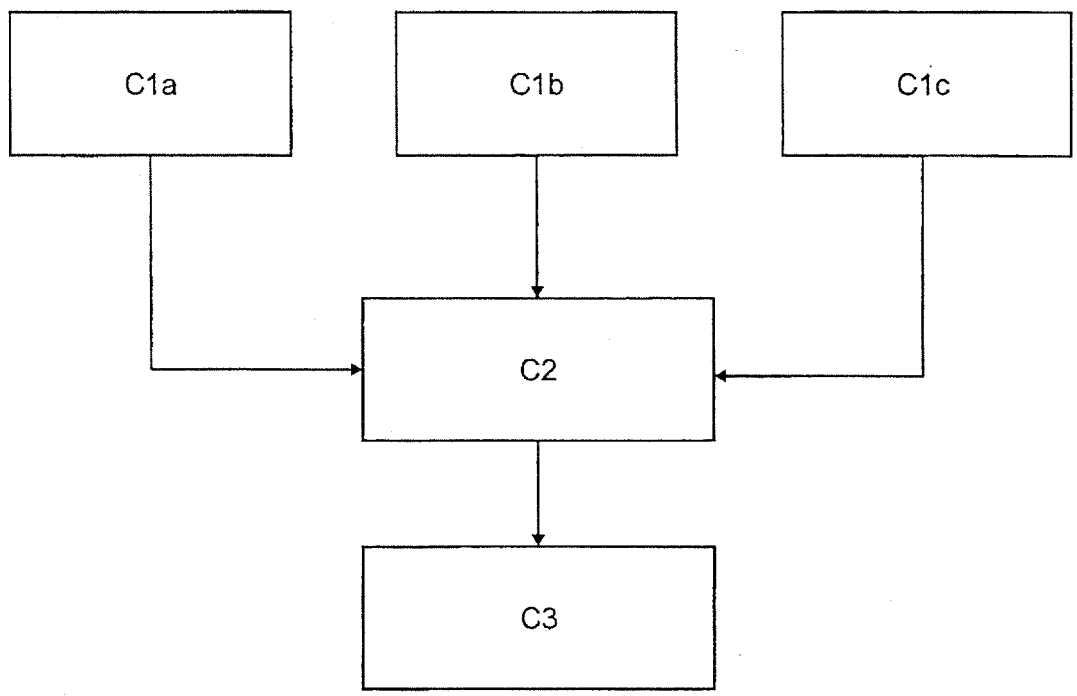
FIG. 3 is a schematic illustration of further details of the course of a method according to further preferred embodiment of the present invention, in particular according to FIG. 2.

A further preferred embodiment of the invention provides a method for optimizing a spectacle lens by using most probable pupil data of an individual eye. The determination of the most probable pupil data of a specific eye according to a preferred embodiment is schematically illustrated in FIG. 3. The most probable pupil data determined in this method is preferably used further in step B1$c$ and is preferably finally taken into account in the optimization of the spectacle lens in step B3. The method is preferably a special case of the method for optimizing a spectacle lens by using most probable data of an individual eye. Individual steps of this preferred method according to FIG. 3 will be described in the following:

Step C1$a$: providing a distribution of the pupil data of a group of eyes, which depends on the parameters brightness, and preferably refraction data and/or other data. Preferably, first of all a distribution of the pupil data of a group of eyes, which depends on the parameters brightness, and is possible also on the refraction data and/or other data, is provided. By analogy with step B1$a$, this distribution can be a sample or in the form of an analytical model. The distribution represents the statistical information on the pupil data and the refraction data and/or the other data of a group of eyes, which is known from a group of eyes.

A possible analytical model of such a distribution is composed of a vector-valued regression function and a multivariately normally distributed regression error see paragraph on the analytical model of the distribution of Zernike coefficients in step B1$a$). Both the regression function and the covariance matrix of the regression error is a vector or matrix-valued function of at least one of the following parameters: the refraction in power vector representation, addition, age, accommodation state, and in particular the brightness or the logarithm of the brightness. The regression function and the covariance matrix are typically obtained by minimizing the error squares of a sample weighted with the covariance matrix. Each component of the regression function can be in the form of a polynomial of the above-mentioned parameters, which is defined section by section, and indicates the average dependence of the pupil data, assigned to this component, on the parameters, e.g. dependence of the pupil size on the brightness and/or dependence of the pupil position relative to the apex of the brightness. In particular, such a function may, in sections, be a constant function, a linear function, or a quadratic function of the parameters.

The multivariately normally distributed regression error may, but does not have to, posses a non-diagonal covariance matrix that can also be a function of the above-mentioned parameters. Such a function (i.e. each element of the covariance matrix), like the regression function itself, can in sections be approximated as a constant function, linear function, or quadratic function of the parameters. If in particular the regression error does not depend on the parameters, then the covariance matrix will be a constant function of the parameters. If there are no statistical relations between individual components of the pupil data, then the covariance matrix will be diagonal.

A special case of the above-described analytical model is the dependence of a single pupil size (here considered as a pupil diameter) on age and brightness, and has been taken from the publication of Winn et al. The regression function $\bar{d}(E_V, a)$ specifies the pupil diameter as a function of the age $a$ and the luminance in the pupil plane $E_V$ in lux. With the latter, the brightness observed by the eye is modelled.

$$\bar{d}(E_V, a) =$$

$$8.95\,\text{mm} - 1.557\,\text{mm} \cdot \log_{10} E_V - 0.0509 \frac{\text{mm}}{\text{year}} \cdot a + 0.0110 \frac{\text{mm}}{\text{year}} \cdot a \log_{10} E_V$$

The standard error, and thus the standard deviation of the distribution of the pupil diameters is $\sigma_d = 1.0$ mm, irrespective of age and luminance. Altogether, the distribution of the pupil diameters is given by $$d(E_V, a) \sim \text{Normal}(\bar{d}(E_V, a), \sigma_d^2)$$

where Normal(x,y) is the normal distribution with expectation value x and variance y.

Another special case relates to the distribution of the change $\partial d/\partial \log_{10} E_V$ in the pupil diameter d per logarithmic luminance $\log_{10} E_V$ depending on the age. According to Winn et al., the distribution is given by $$\frac{\partial d}{\partial \log_{10} E_V} \sim \text{Normal}(PV, \sigma_{PV}^2)$$

with $$PV = -0{,}11 \frac{\text{mm}}{\text{year} \cdot \log_{10} lux} \times \text{age} + 1{,}557 \frac{\text{mm}}{\log_{10} lux}$$

$$\text{and } \sigma_{PV}^2 = 0{,}2 \frac{\text{mm}}{\log_{10} lux}.$$

Step C1$b$: providing refraction data of an eye and/or other data of the same eye, and preferably pupil data of the same eye for at least one brightness. Preferably, is analogous to step B1b, which relates to the provision of refraction data of an eye and/or other data of the eye. If possible, pupil data of the eye for at least one brightness will be provided as well, which can be attained by a measurement with a device or by a manual measurement, for example.

Step C1c: optionally providing at least one functional relation between the parameters of the distribution provided in step C1a and the data of the eye provided in step C1b. Preferably, like in step B1d, functional relations between the parameters of the distribution provided in step C1c, which are not pupil data, and the data used in step C1b, which are not refraction data, are established if required. A possible functional relation is the relation between age and addition mentioned in step B1d.

Step C2: drawing conclusions about the most probable pupil data of said one eye for at least one brightness. Conclusions are drawn on the most probable pupil data of said eye for at least one brightness. The brightness or the brightnesses are at least the brightness present during refraction, as well as further brightnesses required for the optimization of the spectacle lens in step B3. If required, first of all (one or more) functional relations of step C1c are used to convert data provided for the eye in step C1b into the parameters on which the distribution provided in step C1a depends. For example, in this way, the addition included in the refraction data can be converted into an age if the distribution in step C1a is a distribution of the pupil data and age, and the addition of said eye included in the refraction data in step C1b was provided.

If no pupil data or pupil data for only one brightness were provided in C1b, then first a conditional distribution of the brightness-dependent pupil data of a group of eyes will be calculated by evaluating the distribution provided in step C1a for given refraction data and/or other data of an eye. The refraction data and/or other data of said one eye may optionally have been calculated by means of the functional relations provided in C1c.

If the distribution of the brightness-dependent pupil data of a group of eyes is given as a sample, then the conditional distribution will be that part of the sample which with respect to the refraction data and/or other data differs sufficiently little from the refraction data and/or other data of the eye. If the distribution of the brightness-dependent pupil data of a group of eyes is available as an analytical approximation, then the conditional distribution will be calculated by inserting the refraction data and/or other data of said eye into the analytical approximation.

If no pupil data of said eye was provided in C1b, then the most probable pupil data will be identical to the maximum of the conditional distribution of the pupil, evaluated for the corresponding brightnesses. If the distribution is in particular given as an analytical approximation, which is consists of a regression function and a normally distributed regression error, then the most probable pupil data will be given by the value of the regression function into which the refraction data and/or other data of said eye and the corresponding brightnesses were inserted.

However, if pupil of said eye was provided in C1b, then the following cases can be distinguished:

Case 1: providing pupil data for two or more brightnesses. In this case, the most probable pupil data is either the provided pupil data or, if the most probable pupil data is to be determined for other brightnesses, it is calculated by interpolation and/or extrapolation of the provided pupil data. Here, the pupil data depending on the logarithm of the brightness are interpolated or extrapolated linearly or by means of splines. Since the distribution provided in step C1a includes much less information on the pupil data of said eye than the provided pupil data for this eye, the conditional distribution of the pupil data will in this case not be taken into account in the calculation of the most probable pupil data of said eye.

Case 2: providing pupil data for one single brightness. In order to draw conclusions about the pupil data for other brightnesses based on the pupil data provided, the conditional distribution of the brightness-dependent pupil data of a group of eyes is used together with the pupil data provided. Here, the conditional distribution is evaluated on the pupil data provided for said eye, so that a further conditional distribution of the pupil data for at least one brightness results. The most probable pupil data for at least one brightness is given by the maximum of the further conditional distribution for the corresponding brightnesses.

Step C3: using the most probable pupil data of said one eye determined in C2 for calculating a spectacle lens by provision in step B1c. The thus determined most probable pupil data of said one eye for at least one brightness is used to provide it in step B1c. They are thereby taken into account in the optimization of the spectacle lens in step B3.

The invention claimed is:

1. A method for adapting an individual spectacle lens for at least one eye of a spectacle wearer, comprising:
   specifying an individual situation of wear, which comprises at least one brightness target value for light to be captured by the at least one eye;
   determining an individual position, occurring or expected for the at least one brightness target value, of the pupil for at least one direction of sight of the at least one eye;
   determining a reference point of the spectacle lens, in which the spectacle lens causes a correction of individual refraction data required for the at least one direction of sight; and
   providing and arranging the spectacle lens such that the at least one reference point of the spectacle lens is arranged depending on the determined individual value of the position of the pupil, in front of the at least one eye of the spectacle wearer.

2. The method according to claim 1, wherein determining the expected individual position of the pupil and/or determining the individual influence of the brightness on the position and/or size of the pupil comprises:
   setting measurement conditions in which the brightness captured by the at least one eye at least corresponds to a brightness target value specified in the individual situation of wear; and
   detecting the position or size of the pupil of the at least one eye under the measurement conditions set.

3. The method according to claim 1, wherein determining the expected individual position of the pupil and/or determining the individual influence of the brightness on the position and/or size of the pupil comprises:
   specifying a relation between the brightness captured by the at least one eye and the position and/or size of the pupil, wherein the specified relation has at least one individual adaptation parameter;
   identifying a position and/or size of the pupil together with a brightness captured by the at least one eye;
   determining the at least one individual adaptation parameter from the identified position and/or size of the pupil as well as the brightness identified therewith; and
   identifying the individual position and/or size of the pupil expected for the predetermined brightness target value from the specified relation between the brightness captured by the at least one eye and the position and/or size of the pupil by taking the determined individual adaptation parameter into account.

4. The method according to claim 3, wherein the brightness captured by the at least one eye, which is determined together with a position and/or size of the pupil, is measured using a brightness sensor.

5. The method according to claim 3, wherein identifying a position and/or size of the pupil together with a brightness captured by the at least one eye comprises:
   arranging a brightness reference object close to the at least one eye such that the brightness reference object is subjected to the same brightness as the at least one eye;
   collecting image data of the at least one eye together with the brightness reference object; and
   determining the brightness from the representation of the brightness reference object in the image data.

6. The method according to claim 1, wherein determining the expected individual position of the pupil and/or determining the individual influence of the brightness on the position and/or size of the pupil comprises measuring a position of the pupil relative to a coordinate system fixed with respect to the head.

7. The method according to claim 1, wherein determining the expected individual position of the pupil and/or determining the individual influence of the brightness on the position and/or size of the pupil comprises measuring a position or the pupil relative to a marked feature of the at least one eye.

8. The method according to claim 1, wherein determining the expected individual position of the pupil and/or determining the individual influence of the brightness on the position and/or size of the pupil comprises specifying a direction of sight by means of a fixation object and/or a fixation target.

9. The method according to claim 1, wherein a measurement of a position and/or size of the pupil is performed for a first luminance in a range from approximately 3 cd/m$^2$ to approximately 30 cd/m$^2$, and a measurement of a position and/or size of the pupil is performed for a second luminance in a range from approximately 0.003 cd/m$^2$ to approximately 30 cd/m$^2$.

10. The method according to claim 9, wherein the measurement of a position and/or size of the pupil is performed for the second luminance in the range from approximately 0.003 cd/m$^2$ to approximately 3 cd/m$^2$.

11. The method according to claim 10, wherein the measurement of a position and/or size of the pupil is performed for the second luminance in the range from 0.003 cd/m$^2$ to approximately 0.3 cd/m$^2$.

12. The method according to claim 11, wherein the measurement of a position and/or size of the pupil is performed for the second luminance in the range from approximately 0.003 cd/m$^2$ to approximately 0.03 cd/m$^2$.

13. A method for optimizing and producing an individual spectacle lens for at least one eye of a spectacle wearer, comprising:
   specifying an individual situation of wear, which specifies one brightness target value for light to be captured by the at least one eye for each of at least two different reference points of the spectacle lens;
   determining refraction data of the at least one eye for the at least two different reference points;
   determining an individual influence of the brightness of the light captured by the at least one eye on the position of the pupil of the at least one eye; and
   optimizing and producing the spectacle lens, which causes a correction, destined for the reference points, of the refraction data for the positions of the pupil of the at least one eye, which result from the determined influence of the brightness on the position of the pupil for the brightness target values specified for the reference points.

14. The method according to claim 13, further comprising determining an individual size of the pupil respectively occurring or expected for the specified brightness target values, wherein optimizing the spectacle lens comprises minimizing a target function which, for the at least two reference points, evaluates a correction of the refraction data respectively determined for the respective reference point, said correction being caused by the spectacle lens in a surrounding of the respective reference point, wherein the size of the surrounding of the respective reference point is selected depending on the individual size of the pupil determined for the respective reference point.

15. The method according to claim 14, further comprising:
   providing a distribution of refraction data, which describe at least higher-order aberrations, for a plurality of eyes, which differ at least partly in at least one further physical and/or physiological parameter;
   determining a value of the at least one further physical and/or physiological parameter for the at least one eye of the spectacle wearer; and
   determining the most probable values, according to the provided distribution of refraction data, for the higher-order aberrations of the at least one eye of the user for the determined value of the at least one further physical and/or physiological parameter for the at least one eye, wherein the spectacle lens is optimized such that it corrects the higher-order aberrations according to the determined most probable values at least partly.

16. A measuring apparatus for collecting individual user data that specifies at least a position of a pupil of at least one eye, wherein the measuring apparatus comprises:
   an illuminating device adapted to determine a brightness captured by the at least one eye; and
   an image-capturing device adapted to collect image data of the pupil together with a position reference point.

17. The measuring apparatus according to claim 16, further comprising a brightness sensor adapted to measure the brightness captured by the at least one eye.

18. The measuring apparatus according to claim 16, further comprising:
   a data-of-wear detection interface adapted to detect a specification for at least one brightness target value; and
   an illumination control device adapted to control the brightness of the illuminating device such that the light captured by the at least one eye corresponds to the detected brightness target value.

19. The measuring apparatus according to claim 16, further comprising at least one of a fixation target, a fixation object, and a fixation projection device adapted to control the eye's direction of sight.

20. The measuring apparatus according to claim 16, which is designed as at least one of a video centration system, an auto refractometer, an aberrometer, a keratograph, a tonograph, and a pachymeter.

21. A measuring apparatus for collecting individual user data that specifies at least a position of a pupil of at least one eye, wherein the measuring apparatus comprises:

a brightness sensor adapted to measure the brightness captured by the at least one eye; and an image-capturing device adapted to collect image data of the pupil together with a position reference point.

* * * * *

UNITED STATES PATENT AND TRADEMARK OFFICE
CERTIFICATE OF CORRECTION

PATENT NO. : 9,696,563 B2
APPLICATION NO. : 14/365151
DATED : July 4, 2017
INVENTOR(S) : Stephan Trumm et al.

It is certified that error appears in the above-identified patent and that said Letters Patent is hereby corrected as shown below:

On the Title Page

Under item (72) INVENTORS:

Please delete "Rainer Sessner, Rothenburg ob der Tauber (DE)" and insert therefor --Rainer Sessner, Roth (DE)--, Please delete "Helmut Altheimer, Baiswell-Lauchdorf (DE)" and insert therefor --Helmut Altheimer, Baisweil-Lauchdorf (DE)--, Please delete "Wolfgang Becken, Munich (DE)" and insert therefor --Wolfgang Becken, Neuried (DE)--, and Please delete "Wolfgang Hauk, Munich (DE)" and insert therefor --Wolfgang Hauk, Augsburg (DE)--.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*